United States Patent
Boese et al.

(10) Patent No.: US 7,702,064 B2
(45) Date of Patent: Apr. 20, 2010

(54) METHOD FOR PROVIDING 3D X-RAY IMAGE DATA RECORD AND AN X-RAY IMAGING SYSTEM WITH A MEASURING FACILITY FOR DETECTING THE BREATHING PHASE OF A PATIENT

(75) Inventors: Jan Boese, Eckental (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/897,372

(22) Filed: Aug. 30, 2007

(65) Prior Publication Data

US 2008/0056447 A1 Mar. 6, 2008

(30) Foreign Application Priority Data

Aug. 31, 2006 (DE) .................. 10 2006 040 943

(51) Int. Cl.
*G01N 23/00* (2006.01)

(52) U.S. Cl. ................ 378/8; 378/95; 378/115

(58) Field of Classification Search .......... 378/8, 378/91, 95, 114–116

See application file for complete search history.

(56) References Cited

U.S. PATENT DOCUMENTS 6,865,248 B1 * 3/2005 Rasche et al. .......... 378/8

FOREIGN PATENT DOCUMENTS

| DE | 199 46 092 A1 | 3/2001 |
| DE | 10 2005 016 472 A1 | 10/2006 |
| WO | WO 03/084405 A2 | 10/2003 |

* cited by examiner

*Primary Examiner*—Jurie Yun

(57) ABSTRACT

The invention relates to a method for providing a 3D x-ray image data record of a patient, in particular of the heart, by an x-ray imaging system connected to a measuring facility which monitors the breathing phases of the patient. The x-ray image system is automatically activated repeatedly when a predetermined breathing phase is reached and an image acquisition operation is carried out, during which a plurality of 2D x-ray images are recorded. An individual 3D image data record is reconstructed from the 2D x-ray images of each image acquisition operation and the different 3D image data records are registered in pairs in order to assign them in a correct positional and dimensional arrangement. Registration parameters are obtained during the registration. The 3D image data record is reconstructed from 2D x-ray images from all image acquisition operations using the registration parameters.

8 Claims, 2 Drawing Sheets

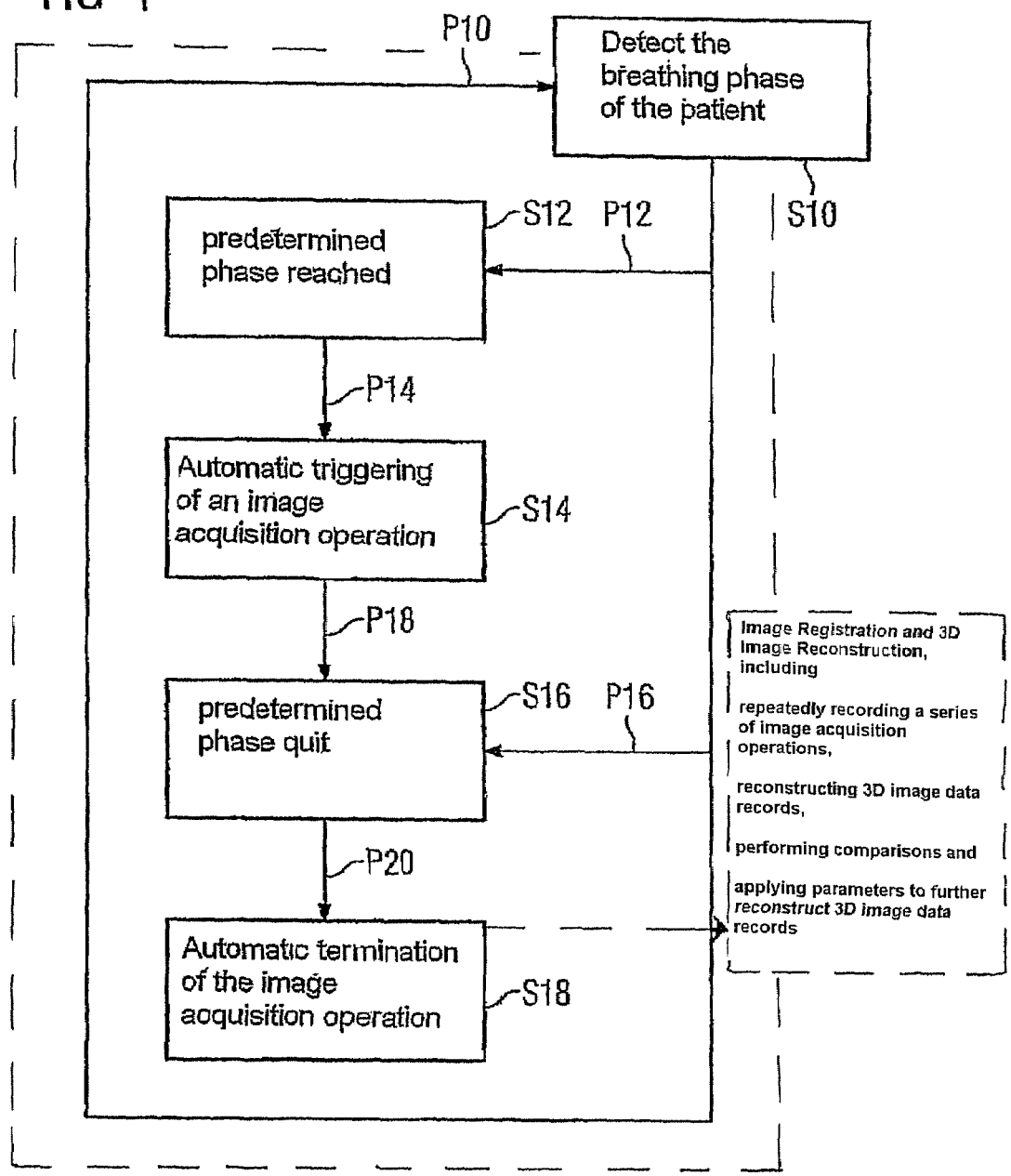

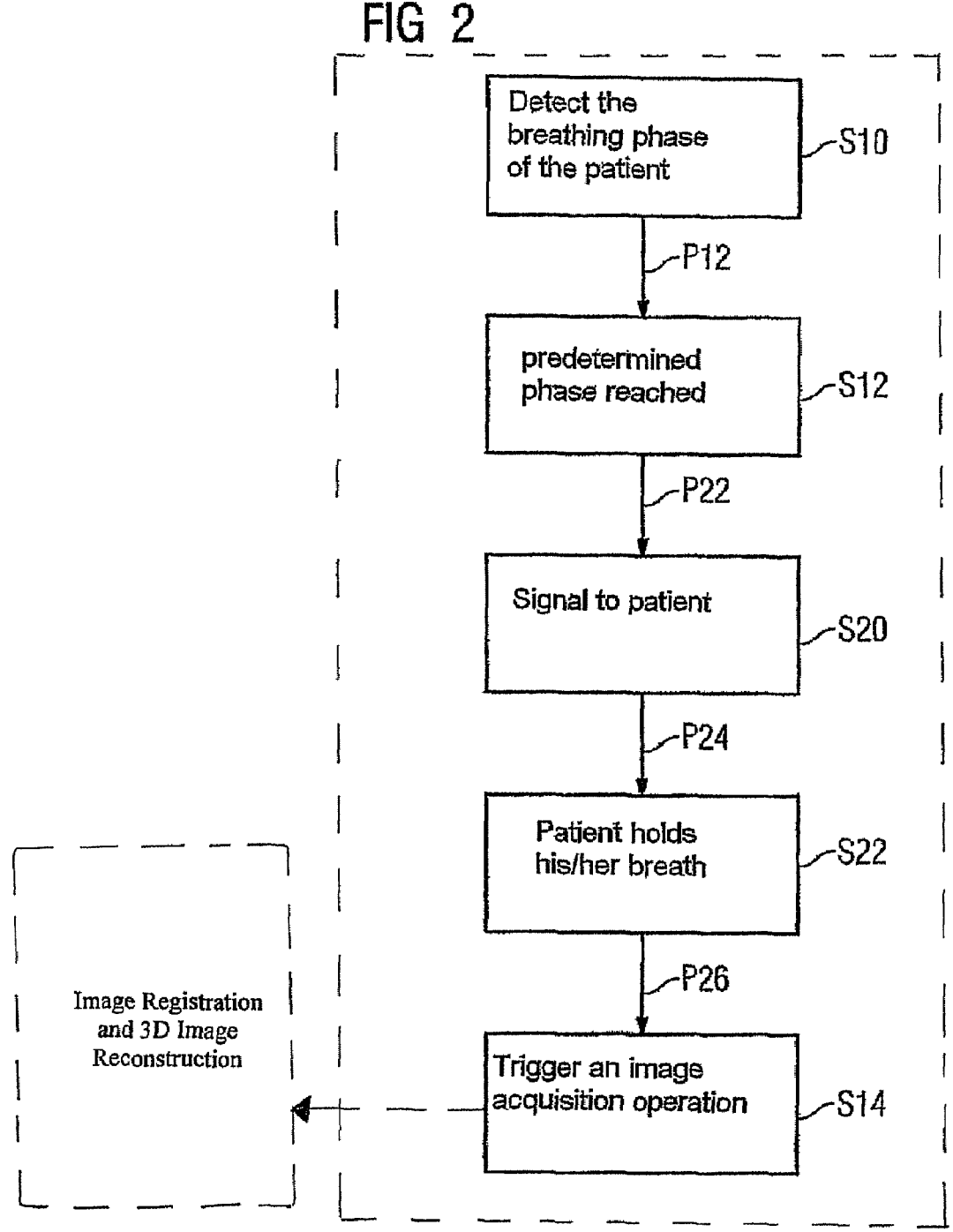

METHOD FOR PROVIDING 3D X-RAY IMAGE DATA RECORD AND AN X-RAY IMAGING SYSTEM WITH A MEASURING FACILITY FOR DETECTING THE BREATHING PHASE OF A PATIENT

CROSS REFERENCE TO RELATED APPLICATIONS

This application claims priority of German application No. 10 2006 040 943.4 filed Aug. 31, 2006, which is incorporated by reference herein in its entirety.

FIELD OF THE INVENTION

The invention relates to a method for providing a 3D x-ray image data record of a patient, in particular of the heart, using an x-ray imaging system, in which the breathing of the patient is monitored repeatedly or continuously by a measuring facility, which is connected to the x-ray imaging system by way of a signal path. The invention also relates to an x-ray imaging system with a measuring facility for detecting the breathing phase of a patient.

BACKGROUND OF THE INVENTION

A C-arm x-ray angiography system is in particular provided as an x-ray imaging system, in particular for the method mentioned in the introduction. The publication DE 10 2005 016 472 published after the application date of the present application discloses in particular a method, wherein a plurality of image acquisition operations is performed with the aid of a C-arm x-ray angiography system. While only one individual image acquisition operation of this type is normally implemented with x-ray angiography, the method described in the said application is characterized in that an electrocardiogram (ECG) of the patient is recorded. A phase of the ECG can herewith be assigned to each x-ray image. Only the x-ray images of a certain heart phase are then selected for the 3D x-ray image data record to be reconstructed, so that the overall image is not "blurred" by the movement of the heart. If necessary, several 3D x-ray image data records can be generated for each specific heart phase. The said method is thus tailored to mapping the heart.

The different image acquisition operations were hitherto run immediately one after the other. A C-arm movement over approximately 200° in approximately 5 seconds is thus carried out with each acquisition operation. Three to four C-arm acquisition operations are necessary. The overall duration of the image recording then typically amounts to 25 seconds. Since not only the movement of the heart can produce image unsharpness, but also the breathing of the patient, the patients are requested to hold their breath during the entire image recording procedure. The entire duration of 25 seconds for this is relatively long and therefore may cause problems in the case of children and patients with breathing problems.

SUMMARY OF THE INVENTION

The object of the invention is to develop the method mentioned at the start such that the patient friendliness is increased and the quality of the 3D x-ray image data record reconstruction is simultaneously good.

The object is achieved by a method and by an x-ray imaging system with the features as claimed in the claims.

The invention relates to a method for providing a 3D x-ray image data record of a patient, in particular of the heart, using an x-ray imaging system, in which the breathing of the patient is monitored repeatedly or continuously by means of a measuring facility, which is connected to the x-ray imaging system by way of a signal path. A distinction is herewith made between different breathing phases and the x-ray imaging system is automatically activated repeatedly once a predetermined breathing phase has been reached, and performs an image acquisition operation, during which a plurality of 2D x-ray images are recorded from different perspectives with the aid of the x-ray imaging system and with an image acquisition operation-encompassing 3D x-ray image data record being generated from the 2D x-ray images from all the image acquisition operations by means of a reconstruction method.

The method according to the invention is thus herewith characterized in that an individual 3D image data record is reconstructed in each instance from the 2D x-ray images of each image acquisition operation, and that the different 3D image data records are registered with one another in pairs, in order to assign these to one another in a correct positional and dimensional arrangement, with registration parameters being obtained during the registration, said registration parameters being used during the calculations of the subsequent reconstruction of the image acquisition operation-encompassing 3D image data record. An image acquisition operation is then triggered repeatedly when a predetermined breathing phase is reached.

The invention is based on the knowledge that not all image acquisition operations need to be performed temporally immediately one after the other. Instead, an image acquisition operation is regarded as a natural "element", for which the patient is prepared again in each instance. In particular, the patient may breathe between the image acquisition operations. With the above-mentioned time duration of an image acquisition operation of 5 seconds, the patient must only hold his/her breath for 5 seconds.

As the process of holding one's breath and repeatedly holding one's breath is repeated a number of times, provision can routinely be made for an acoustic or optical signal to be output when the predetermined breathing phase is reached (by means of a measuring facility or alternatively by means of the x-ray imaging system, if the latter is connected to the measuring facility), by means of which to the patient is requested not to continue the breathing process during the image acquisition operation. It is essentially possible for the treating doctor to request that the patient holds his/her breath. The doctor would then nevertheless have to be informed about the breathing phase having been reached, and would similarly have to receive a signal. It is then easier if the patient responds to the signal directly.

The doctor can essentially also be involved in the start of the image acquisition operation. This then obliges him to check whether the patient is actually not continuing to breath, and in this case, to trigger an image acquisition operation (e.g. by pressing a button on the x-ray imaging system). The measuring facility is however preferably connected to the x-ray imaging system by way of an (electrical) signal path (i.e. a line). When the predetermined breathing phase has been reached, the x-ray imaging system is to be automatically activated and the image acquisition operation is to be carried out. The type of signal which flows over the electrical signal path is irrelevant here. It either concerns the measuring signals themselves, which are provided by the measuring facility, and which are then evaluated by a data processing facility in the x-ray imaging system. Alternatively, the measuring facility also comprises a data processing facility and emits a control signal to the x-ray imaging system when the predetermined breathing phase has been reached.

If an image acquisition operation is triggered once, a first alternative then provides for a predetermined number of 2D x-ray images to be recorded in any case, irrespective of whether or not the patient subsequently holds his/her breath. With a second alternative, the breathing is monitored further during the image acquisition operation. If the predetermined breathing phase is left, the x-ray imaging system is then automatically triggered to terminate the image acquisition operation. It is self-explanatory in the latter alternative that the breathing phase needs to be defined via a sufficiently wide interval of measured values of the measuring facility, so that the termination of the image acquisition operation is not immediately effected by all small changes in the measured values. The second alternative is advantageous in that all images are only assigned to the predetermined breathing phase. The first alternative is advantageous in that the number of 2D x-ray images can be the same with each image acquisition operation, thereby simultaneously facilitating the data processing.

To ensure that the patient breaths between the different image acquisition operations, it may happen, despite the measurement by the measuring facility, that the x-ray images are not all recorded in the same breathing phase. As a result of the duration of the image recording, which is overall longer, it can also happen that the patient moves on the patient bed. As is known, to compensate for the series of movements, so-called registration methods can be used. During a registration, emphasized structures in the images are recognized by automatic image recognition, and a comparison between a first data record and a second data record determines how the position of the emphasized structures has changed. The dimensions can also change. Such a registration currently lends itself to a preferred embodiment of the method, wherein an individual I3D image data record is reconstructed from the 2D x-ray images of each image acquisition operation, and wherein the 3D image data records are registered with one another in pairs. During the registration, registration parameters are obtained. These represent a mapping of one data record onto the other. The registration parameters can be used with calculations within the scope of a subsequent reconstruction of an image acquisition operation-encompassing 3D image data record (from the previous plurality of 3D image data records). Six registration parameters are conventionally obtained for six degrees of freedom. If one additionally wants to consider that many mapped body structures are compressed and expanded again (e.g. which is naturally the case with the heart), an elastic 3D/3D registration method can also be used, within the scope of which a so-called movement field is determined. In the case of a movement field, an arrow is specified at each site, the direction of which specifies the direction of the expansion or compression of the object, and the length of which specifies the extent of the expansion or compression.

As mentioned at the start, the method of the present invention is suited in particular to extending the method to be inferred from the above-mentioned DE 10 2005 016 472. If the image structures which are dependent on the heartbeat of the patient are mapped in the x-ray images, e.g. the heart itself the heartbeat phase of the patient can be monitored by means of a second measuring facility, a heartbeat phase can be determined for each x-ray image and assigned to the x-ray image. If necessary, a number of 3D image data records can then be obtained, which are assigned in each instance to a heartbeat phase.

The x-ray imaging system according to the invention is preferably a C-arm x-ray angiography system. It is connected to a measuring facility by way of a signal line, said measuring facility detecting the breathing phases of a patient, and is designed here to implement (and/or introduce) an x-ray image acquisition operation, wherein a number of x-rays are recorded from different perspectives, by virtue of a signal received by way of the signal line. It is again the case here that the signals received over the signal line can be direct measurement signals from the measuring facility, which are evaluated by a data processing facility in the x-ray imaging system. Instead, the measuring facility can also have its own data processing facility, which evaluates the measurement signals and outputs a control signal to the x-ray imaging system. The actual x-ray imaging system then only needs to have one data processing unit, which is programmed such that an x-ray image acquisition process is begun and implemented when a control signal is received.

According to a further aspect of the invention, provision is made for a measuring facility for detecting the breathing phase of a patient using an evaluation unit, and also comprises a signal output unit outputting an acoustic and/or optical signal. The evaluation unit is designed to trigger a signal output by means of the signal output unit when detecting a predetermined breathing phase.

A three-dimensional position sensor, such as is known inter alia from the company Biosense Webster, Diamondbar, Calif., USA, can be used as a measuring facility for detecting the breathing phase of a patient for instance within the scope of the present invention. Another type of measuring facility is also a breathing belt, as came onto the market for instance from the company Pasco, Roseville, Calif., USA. The three-dimensional position sensor or breathing belt measures the breathing-specific expansion of the chest of the patient. As an alternative to expanding the chest, the breathing activity can be measured on the basis of the quantity or composition of exhaled air. A sensor which is suited to this is known for instance from the company Optovent AB, Linköping, Sweden.

All these types of measuring facilities can be provided with the above-mentioned evaluation unit and the signal output unit.

BRIEF DESCRIPTION OF THE DRAWINGS

Preferred embodiments of the invention are described below with reference to the drawings, in which:

FIG. 1 shows a schematic representation of the sequence with a first embodiment of the method according to the invention and FIG. 2 shows a schematic representation of the sequence with a second embodiment of the method according to the invention.

DETAILED DESCRIPTION OF THE INVENTION

The invention allows for numerous embodiments. While a first embodiment and a second embodiment are described with reference to FIG. 1 and FIG. 2 respectively, other hybrid, shortened and extended forms are also conceivable.

It is common to the embodiments that a patient is located in a C-arm x-ray angiography system, and that a plurality of image acquisition operations is carried out, wherein x-ray images of the heart of the patient are to be obtained in each case. An ECG is recorded concomitantly, so that a heartbeat phase can be assigned in each instance to the x-ray images. Details relating to a method of this type are described in the above-mentioned publication DE 10 2005 016 472 which was published after the application day of the present application.

The sequence illustrated in FIG. 1 and FIG. 2 is common such that the breathing phase of the patient is detected, see S10. As shown by the arrow system with the arrow P10, provision is made with the sequence according to FIG. 1 that the breathing phase of the patient is continuously detected. A predetermined phase is reached (see arrow P12) at any time step S12. If, for instance, the measuring facility detects the expansion of the chest of the patient while breathing, the predetermined phase can correspond to a maximum expansion of the chest ("fully inhaled"). A percentage of this maximum expansion can also be meaningful to the definition. A portion of 90° chest expansion (calculated by way of an interval between the maximum and the minimum chest expansion) can be defined as the predetermined phase for instance. In the latter case, the patient is allowed to exhale a little more air before he discontinues the breathing process.

As shown in FIG. 1 by the direct arrow P14, after the predetermined phase has been reached in S12, an image acquisition operation is automatically triggered, see S14. To enable such an automatic triggering of an image acquisition operation, the measuring facility, with the aid of which the breathing phase of the patient is detected (S10), must be connected in any way to the C-arm x-ray angiography system by signals, said C-arm x-ray angiography system having to carry out the image acquisition operation.

The sequence illustrated in FIG. 1 is in this respect patient-friendly in as much as the patient is not induced to hold his/her breath in a particularly strict manner. Instead, the breathing phase of the patient (S10) is continuously detected, and as shown by the arrow P16, it is determined when the predetermined phase is quit, with this being illustrated here by the presence of the arrow P18 such that this quitting takes place after the triggering of the image acquisition operation in step S14, namely in step S16. The image acquisition operation is subsequently (see arrow P20) automatically terminated, see S18. The steps can be repeated as often as required, and in particular the breathing phase of the patient is indeed continuously detected (see once again arrow P10), and each passage re-determines that the predetermined phase is reached (arrow P12; step S12), and an image acquisition operation is then retriggered each time (step S14). The steps S16 and S18 do not necessarily terminate the image acquisition operation. If the predetermined phase is not quit until a predetermined number of images has been recorded within the scope of the image acquisition operation, the acquisition operation can already be terminated of its own accord and need no longer be triggered by quitting the predetermined phase.

Also with the sequence illustrated in FIG. 2, the breathing phase of the patient is detected (S10) first and then it is temporally determined (arrow P12) that the predetermined phase has been reached (see step S12). In the case of this embodiment, the breathing phase of the patient need not be constantly detected, but the detection can be interrupted, after step 12 has been reached. Step S12, see arrow P22, moves to emitting a signal to the patient, step S20. A signal of this type can be an acoustic or optical signal or a combination of such signals. Step S20 is to be carried out immediately after step S12, so that the transition to step S22 can be made as quickly as possible according to arrow P24, in which step the patient holds his/her breath. The patient is to hold his/her breath as a far as possible during the predetermined phase. A transition is made here to step S14', according to arrow P26, in which step an image acquisition operation is triggered. The transition according to arrow P26 can be designed such that a doctor operating the C-arm x-ray angiography system observes the patient and presses a corresponding trigger button when the patient is actually holding his/her breath. Also in the case of FIG. 2, an image acquisition operation can however also be triggered automatically. In this case, it would be advantageous if step S10 were repeated after step S22 (or as in the case of FIG. 1 constantly repeated), so that a check is automatically carried out as to whether the patient is actually holding his/her breath.

The embodiment according to FIG. 2 does not show how the image acquisition operation is terminated. The standard case is that an image acquisition operation is performed using a predetermined number of x-ray images. The embodiment in FIG. 2 can however also be linked to FIG. 1, in as a far as an automatic termination of the image acquisition operation can be triggered by quitting the predetermined phase. The breathing phase of the patient S10 would then have to be constantly detected.

Conversely, the sequence from FIG. 1 can be extended by step S20 without having to follow step S22. In this case, it would be assumed that a signal to the patient is sufficient, with it being left up to the patient whether or not to actually hold his/her breath. An image acquisition operation would be performed if necessary, which is rapidly interrupted again, or with which the obtained images are not used for the subsequent method.

The sequences which occur naturally are not shown in the figures: A 3D x-ray image data record is generated by the use of reconstruction methods known per se, from the x-ray images, which are no more than 2D image data records obtained with the aid of an x-ray flat screen detector. Different image representations can be obtained from the 3D x-ray image data record by corresponding calculations, said image representations namely being perspective representation or also "cutouts", in other words representations which equate again to the 2D x-ray images.

The invention claimed is:

1. A method for providing a 3D x-ray image data record of an examination area of a patient by an x-ray imaging system, comprising:
   monitoring a plurality of different breathing phases of the patient with a measuring unit connected to the x-ray imaging system;
   automatically activating the x-ray imaging system repeatedly each time a predetermined breathing phase occurs;
   repeatedly recording a series of image acquisition operations each time the imaging system is activated wherein during each image acquisition operation a plurality of 2D x-ray images of the examination area are acquired from multiple different perspectives by the activated x-ray imaging system;
   reconstructing a series of 3D image data records from each series of the 2D x-ray images;
   performing comparisons among pairs of the 3D image data records to determine how position and a dimension of an imaged structure has changed between data records and generating mapping parameters based on the comparisons; and
   then applying the mapping parameters to map data records onto one another to further reconstruct multiple ones of the 3D x-ray image data records from multiple series of the 2D x-ray images.

2. The method as claimed in claim 1, wherein an acoustic or optical signal is emitted when the predetermined breathing phase is achieved to inform the patient holding a breathing during the recording.

3. The method of claim 1, wherein each series of the 2D x-ray images comprises a predetermined number of 2D x-ray images.

4. The method of claim 1, wherein the x-ray imaging system is automatically triggered to terminate the recording when the predetermined breathing phase is over.

5. The method of claim 1, wherein a heartbeat phase of the patient is monitored by a second measuring unit and is assigned to each of the 2D x-ray images.

6. The method of claim 1, wherein the breathing phases of the patient are repeatedly or continuously monitored by the measuring unit.

7. The method of claim 1, wherein a correct positional and dimensional arrangement is assigned a further reconstructed 3D image data record.

8. The method of claim 1, wherein the examination area of the patient is a heart of the patient.

* * * * *